(12) United States Patent
Lazdunski et al.

(10) Patent No.: US 8,063,054 B2
(45) Date of Patent: Nov. 22, 2011

(54) METHOD OF TREATMENT OF RETINAL ISCHEMIA WITH DIAZOXIDE

(75) Inventors: Michel Lazdunski, Nice (FR); Mohamed Ettaiche, Aspremont (FR)

(73) Assignees: Centre National de la Recherche Scientifique-CNRS, Paris (FR); Universite de Nice-Sophia Antipolis, Nice (FR)

( * ) Notice: Subject to any disclaimer, the term of this patent is extended or adjusted under 35 U.S.C. 154(b) by 326 days.

(21) Appl. No.: 11/220,504

(22) Filed: Sep. 7, 2005

(65) Prior Publication Data

US 2006/0025386 A1   Feb. 2, 2006

Related U.S. Application Data

(63) Continuation of application No. PCT/FR2004/000584, filed on Mar. 11, 2004.

(30) Foreign Application Priority Data

Mar. 11, 2003   (FR) ..................................... 03 03011

(51) Int. Cl.
*A61K 31/505*   (2006.01)
(52) U.S. Cl. ....................................... 514/258; 514/912
(58) Field of Classification Search .................. 514/258, 514/912
See application file for complete search history.

(56) References Cited

FOREIGN PATENT DOCUMENTS

| EP | 0 956 866 A1 | 11/1999 |
| WO | WO 94/25033 A1 | 11/1994 |
| WO | WO 99/42103 A1 | 8/1999 |

OTHER PUBLICATIONS

Henri Bernardi, et al. "ATP/ADP Binding Sites are Present in the Sulfonylurea Binding Protein Associated with Brain ATP-sensitive K+ channels" Biochemistry. Jul. 14, 1992;31(27):6328-32.
S. Celebi, et al. "Effects of Melatonin, Vitamin E and Octreotide on Lipid Peroxidation During Ischemia-Reperfusion in the Guinea Pig Retina" Eur J Ophthalmol. Mar.-Apr. 2002;12(2):77-83.
Hsiao-Ming Chao, et al. "Topically Applied Clonidine Protects the Rat Retina from Ischaemia/Reperfusion by Stimulating Alpha(2)-Adrenoceptors and not by an Action on Imidazoline Receptors" Brain Res. Jun. 15, 2001 15;904(1):126-36.
Pedro Cuevas, et al. "Systemic Administration of Acidic Fibroblast Growth Factor Ameliorates the Ischemic Injury of the Retina in Rats" Neurosci Lett. Oct. 9, 1998;255(1):1-4.
John E. Donello, et al. "Alpha(2)-Adrenoceptor Agonists Inhibit Vitreal Glutamate and Aspartate Accumulation and Preserve Retinal Function after Transient Ischemia" J Pharmacol Exp Ther. Jan. 2001;296(1):216-23.
Fabrice Duprat, et al. "The Neuroprotective Agent Riluzole Activates the Two P Domain K(+) channels TREK-1 and TRAAK" Mol Pharmacol. May 2000;57(5):906-12.
Mohamed Ettaiche, et al. "Riluzole Improves Functional Recovery after Ischemia in the Rat Retina" Invest Ophthalmol Vis Sci. Mar. 1999;40(3):729-36.
Mohamed Ettaiche, et al. "ATP-Sensitive Potassium Channels (K(ATP)) in Retina: A Key Role for Delayed Ischemic Tolerance" Brain Res. Jan. 26, 2001;890(1):118-29.
Valerie Fontaine, et al. "Neurodegenerative and Neuroprotective Effects of Tumor Necrosis Factor (TNF) in Retinal Ischemia: Opposite Roles of TNF Receptor 1 and TNF Receptor 2" J Neurosci. Apr. 1, 2002;22(7).
Catherine Heurteaux, et al. "K+ Channel Openers Prevent Global Ischemia-Induced Expression of c-fos, c-jun, Heat Shock Protein, and Amyloid Beta-Protein Precursor Genes and Neuronal Death in Rat Hippocampus" Proc Natl Acad Sci U S A. Oct. 15, 1993;90(20):9431-5.
Neville N. Osborne, et al. "Topical Flunarizine Reduces IOP and Protects the Retina Against Ischemia-Excitotoxicity" Invest Ophthalmol Vis Sci. May 2002;43(5):1456-64.
Gail M. Seigel, et al. "Inhibition of Neuroretinal Cell Death by Insulin-Like Growth Factor-1 and its Analogs" Mol Vis. Aug. 31, 2000;6:157-63.
Marta E. Szabo, et al. "Antioxidant Properties of Calcium Dobesilate in Ischemic/Reperfused Diabetic Rat Retina" Eur J Pharmacol. Oct. 5, 2001;428(2):277-86.
Wolf A. Lagreze, et al. "The Neuroprotective Properties of Gabapentin-Lactam" Graefes Arch Clin Exp Ophthalmol. Nov. 2001;239(11):845-9.
M. W. Hankins et al., *Consequences of Transient Retinal Hypoxia on Rod Input to Horizontal Cells in the Rat Retina*, Vision Research, vol. 33, No. 4, Great Britain, Mar. 1993, pp. 429-436.
Frances M. Ashcroft et al., *New windows on the mechanism of action of KATP channel openers*, Trends in Pharmacological Sciences, Elsevier Trends Journal, vol. 21, No. 11, Cambridge, Great Britain, Nov. 1, 2000, pp. 439-445.

*Primary Examiner* — Zohreh Fay
(74) *Attorney, Agent, or Firm* — Oblon, Spivak, McClelland, Maier & Neustadt, L.L.P.

(57) ABSTRACT

A composition including diazoxide (7-chloro-3-methyl-2H-1,2,4-benzothiadiazine-1,1-dioxide) for the treatment and/or prevention of retinal ischemia and of diseases associated with retinal ischemia. The composition can also contain riluzole, a derivative active in neuroprotection of the latter, or a pharmaceutically acceptable salt of the latter.

7 Claims, 3 Drawing Sheets

METHOD OF TREATMENT OF RETINAL ISCHEMIA WITH DIAZOXIDE

RELATED APPLICATION

This is a continuation of International Application No. PCT/FR2004/000584, with an international filing date of Mar. 11, 2004 (WO 2004/082582 A2, published Sep. 30, 2004), which is based on French Patent Application No. 03/03011, filed Mar. 11, 2003.

FIELD OF THE INVENTION

This invention relates to the use of diazoxide (7-chloro-3methyl-2H-1,2,4-benzothiadiazine-1,1-dioxide) in the treatment of retinal ischemia. The invention relates more particularly to the use of a composition containing diazoxide intended for the treatment and/or the prevention of a retinal ischemia and diseases associated with retinal ischemia.

BACKGROUND

The phenomena leading to the cellular death of the retina and, as a consequence, the loss of visual function are phenomena that occur in processes as varied as ischemias and visible radiation. The chronic development of a state of ischemia in pathologies such as diabetic retinopathy, retinopathy engendered by radiation and damage consecutive to a venous occlusion results in a disturbance of the depolarization of the cellular membrane, which entails, over time, an irreversible destruction of the retina.

Thus, retinal ischemia is observed in the clinic in acute situations such as arterial or venous occlusions of the retina, ocular contusions and also in chronic pathologies such as senile macular degeneration (DMLA), glaucoma, diabetic retinopathy, premature infant retinopathy, and inflammatory diseases and hemopathies that lead to retinal damage even resulting in a number of cases in a total degeneration of the retina. Glaucoma and senile macular degeneration have become the principal causes of poor vision in Western countries, are related to an increase in life expectancy and therefore constitute a real problem for public health.

On account of the frequency and severity of these ocular afflictions there is a real need for an effective treatment for treating and/or preventing diseases associated with retinal ischemia.

In order to counteract damage following a retinal ischemic reperfusion, several pharmacological approaches have been used in experiments. The trappers of free radicals (Celeci et al., 2002; Szabo et al., 2001), the antagonists of glutamate receptors (Lagreze et al., 2001) and adrenergic receptors (Donello et al., 2001; Chao et al., 2001), but also neurotrophic factors (Fontaine et al., 2002; Seigel et al., 2000; Cuevas et al., 1998), calcium channel blockers (Osborne et al., 2002) and inhibitors of the synaptic release of glutamate (Ettaiche et al., 1000) have been proposed as therapeutic agents for the treatment of retinal ischemia. The use of a releaser of glutamate and, more particularly, reluzole in the treatment of retinal ischemia is disclosed in WO 99/42103.

Ischemia induced by an increase of ocular pressure is the model most frequently used for simultaneously studying the mechanisms and potential therapies of retinal ischemia. The degree of the lesion of the retina is a function of the animal species, the duration and the intensity of the ocular pressure imposed. Contrary to the experimental model of retinal ischemia by ligature of the optic nerve, this technique allows, on the one hand, the avoidance of an intraocular hemorrhage consecutive to the beginning of a reperfusion and, on the other hand, offers the advantage of retaining the extraocular structures intact, thus allowing the realizing of local applications of pharmacological substances.

The various pharmacological approaches, validated on experimental animal models, met with two difficulties, namely, on the one hand, the protective, but non-therapeutic aspect of these molecules (with the exception of riluzole) and, on the other hand, their clinical use, which necessitates an administration devoid of any secondary effect on the other organs. The various administration paths used are intravitreous injection and oral, systemic and local paths. The intravitreous injection used for the growth factors can aggravate the inflammatory reaction consecutive to an ischemia but also induce a cellular proliferation at the injection site. The oral path has the problem of the bioavailability of the active principle at the level of the action site, the systemic injection can induce secondary effects on other organs and, finally, the local application can also induce adverse effects on the other ocular tissues, in particular, the loss of corneal sensitivity and a mydriasis.

SUMMARY OF THE INVENTION

This invention relates to a method of treating or preventing a disease associated with retinal ischemia including administering a therapeutically effective amount of a pharmaceutical composition including diazoxide (7-chloro-3-methyl-2H-1,2,4-benzothiadiazine-1,1-dioxide) to a mammal.

DETAILED DESCRIPTION

Figure 1:
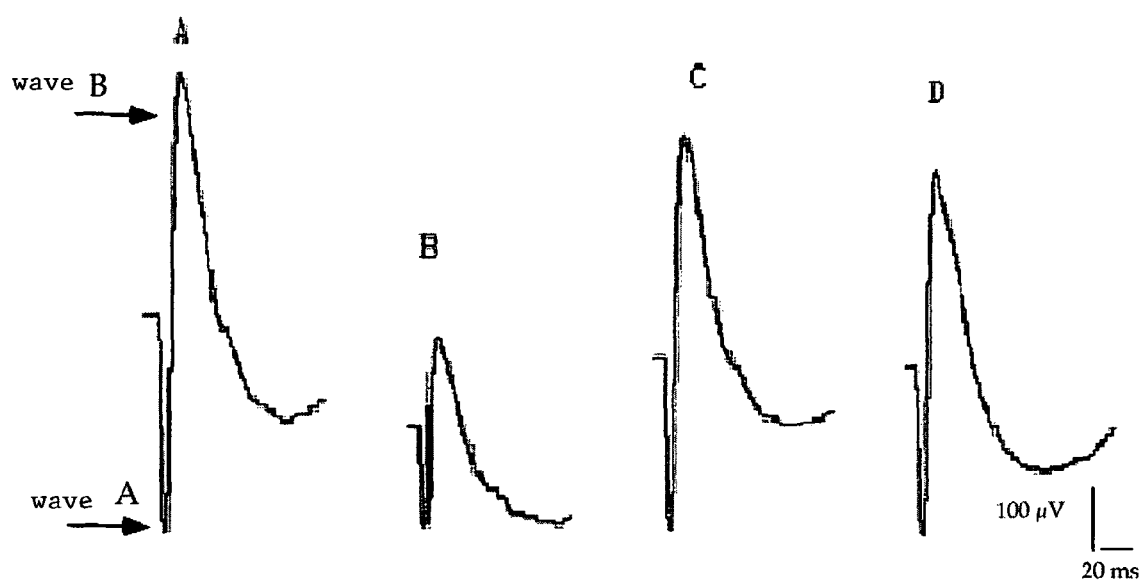
FIG. 1 is a series of representative profiles of electroretinograms recorded in different groups seven days after the end of retinal ischemia.

Our studies demonstrated that certain effects are not observed after the instillation of diazoxide. Our studies also demonstrated that the retina is rich in a class of potassium channels (Ettaiche et al., 2001) that connects the electrical properties of the excitable cells to the metabolism and more particularly to the ATP/ADP ratio (Bemardi et al., 1992). These are the ATP-dependent the potassium channels or KATP channels. In another connection, the activation of the KATP channels by specific openers protects the hippocampus and the central nervous system against ischemia (Heurteaux et al.; 1993). It was from this point of view that diazoxide (7-chloro-4-methyl-2H-1,2,4-benzothiadiazine-1,1-dioxide), an opener of ATP-dependent potassium channels (Ashcroft et al., 2000) was tested on an experimental model of ischemic reperfusion of the retina.

Diazoxide is a pharmaceutical substance developed originally in the treatment of hypertension. Diazoxide is also known to cause a transitory hyperglycemia due to a diminution of the secretion of insulin and to a diminution of the peripheral use of glucose (Henquin et al., 1982, Diabetes 31: 776-783). WO 94/25033 describes a method for treating a deficiency in the metabolism of glucose consisting in administering diazoxide.

Furthermore, diazoxide is a liposoluble substance with a low molecular weight and can therefore traverse the animal or human corneal barrier. Its formulation and conditioning in collyrium can be readily realized, which constitutes a great advantage from the therapeutic and economical point of view in the treatment and/or prevention of diseases associated with retinal ischemia.

We identified a method for preventing the deleterious effects undergone by the neurosensorial retina following an ischemia experimentally induced by elevation of the intraocular pressure. The therapeutic treatment comprises local instillation in the conjunctival sac of a drop of an ophthalmic solution whose active principle is diazoxide. This treatment prevents the loss of visual function by reducing the deleterious effects induced by ischemic reperfusion in the ganglionic, internal plexiform and internal nuclear layers.

Retinal ischemia induced experimentally by increasing the intraocular pressure is the most currently used model for screening molecules and the study of mechanisms involved in ischemia. This model, applied to the rat, whose vascularization of the retina is identical to that of a human, engenders localized lesions in a first phase at the level of the layers of the ganglionic cells and of the internal plexiform. These lesions are expressed by the death of the ganglionic cells and a significant reduction of the thickness of the internal plexiform layer. The second phase is characterized by a reduction of the thickness of the internal nuclear layer as well as of the layer of photoreceptor cells. Topical application of diazoxide after the end of the ischemia or subsequently (24 hours after the start of the reperfusion) blocks the lesions engendered by the ischemic reperfusion in a spectacular manner. This effect is expressed at the level of the visual functioning by a better recovery of the amplitude of the A and B waves, consequence of a good preservation of the cytoarchitecture of the retina. These results (therapeutic effect by local application) designate diazoxide as a molecule with a great therapeutic ability against retinal ischemia and the diseases associated with retinal ischemia.

Consequently, this invention relates to a pharmaceutical composition comprising diazoxide (7-chloro-3-methyl-2H-1,2,4-benzothiadiazine-1,1-dioxide) intended for the treatment and/or the prevention of a disease associated with retinal ischemia.

The pharmaceutical composition advantageously comprises about 0.001% to about 0.1% diazoxide. In this composition, the diazoxide is found in a pharmaceutically applicable vehicle. Within the framework of an ocular application of this composition, those skilled in the art know which vehicles are pharmaceutically acceptable such as, by way of example and in a non-exhaustive manner, sterile physiological serum.

Diabetic retinopathies or those induced by radiation in retinal damage caused by ischemia (multifactorial phenomenon) result from complex mechanisms. As a consequence, association of several molecules having different therapeutic targets and, therefore, different therapeutic virtues should permit a better recovery of the retinal function.

From this point of view, riluzole (2-amino-6-trifluoromethoxy benzothiazole), whose principal property is inhibiting the presynaptic release of glutamate (Ettaiche et al., 1999) via the activation of other types of potassium channels and the TREK and TRAAK channels (Duprat et al., 2000), whose therapeutic effects by local application have been demonstrated experimentally, would be a molecule of choice to be associated with diazoxide in pathologies induced by retinal ischemias.

The terms "derivative active in neuroprotection of riluzole" and "a pharmaceutically acceptable salt of riluzole" denote the molecules described in WO 99/42103. Those skilled in the art can select, if necessary, the form best adapted to the new application in accordance with this invention. The following can be cited in particular as pharmaceutically acceptable salts: Addition salts with mineral acids such as chlorohydrate, sulfate, nitrate, phosphate and the like or organic salts such as acetate, propionate, succinate, oxalate, benzoate, fumarate, maleate, methane sulfonate, isetionate and the like or their substitution derivatives.

The pharmaceutical compositions comprise at least diazoxide in free form or in the form of an addition salt with a pharmaceutically acceptable acid in the pure state or in the form of a composition in which this active agent is associated with any other pharmaceutically compatible product. The drugs in accordance with the invention can be used orally, parenterally, rectally, topically or in any other suitable form.

Examples of solid compositions that can be used for oral administration are pills, powders and the like in which the diazoxide is mixed with one or several classically used inert diluents and possibly with other substances such as, e.g., a lubricant, colorant, coating and the like.

Examples of liquid compositions that that can be used for oral or ocular administration are pharmaceutically acceptable suspensions, solutions, dispersions, emulsions, syrups containing classically used inert diluents and, optionally, other substances such as wetting agents, sweeteners, thickening agents and the like.

The sterile compositions for parenteral administration can be aqueous or non-aqueous solutions, suspensions or emulsions. For solvent or vehicle, water, propylene glycol, vegetal oils or other suitable organic solvents can be used. These compositions can also contain adjuvants such as wetting agents, isotonic agents, emulsifiers and the like.

The compositions for topical administration can be, e.g., creams, lotions, "collutoires", nasal or ocular drops or an aerosol.

As appears from the Examples below, a preferred form of the pharmaceutical composition used is a local application into the eye of the drug. This application into the eye is advantageously a local instillation into the conjunctival sac. The local application into the eye constitutes an advantageous manner of using diazoxide. Thus, a pharmaceutical composition can be envisioned that presents itself in particular in the form of a collyrium.

The invention also relates to the process for preparing drugs comprising mixing diazoxide, optionally with riluzole, a derivative active in neuroprotection of the latter, a pharmaceutically acceptable salt of the latter, with one or several compatible and pharmaceutically acceptable diluents and/or adjuvants.

The invention also relates to a method for treating and/or preventing a disease associated with a retinal ischemia comprising administering a therapeutically effective amount of a pharmaceutical composition such as described above to a patient suffering from or who might suffer from this disease.

The term "disease associated with a retinal ischemia" denotes a disease selected from the group constituted of arterial or venous occlusions of the retina, ocular contusions and also in chronic pathologies such as senile macular degeneration (DMLA), glaucoma, diabetic retinopathy, premature infant retinopathy, inflammatory diseases and hemopathies.

Other advantages and characteristics of the invention will be apparent from the following examples relating to the study of the effects of a diazoxide treatment on rats caused to have ischemia. These examples are given by way of illustration and are not to be interpreted as limiting the scope of the invention as defined in the appended claims. They make reference to the attached figures.

FIG. 1 relates to representative profiles of electroretinograms recorded in the different groups tested (A to D) 7 days after the end of the retinal ischemia. FIG. 1A corresponds to the control group (control rats not caused to have ischemia and non-treated), FIG. 1B corresponds to the group of rats that underwent an ischemia of 40 min but were not treated, FIG. 1C corresponds to the group of rats treated by diazoxide applied 30 min after the end of the ischemia and FIG. 1D corresponds to the group of rats treated by diazoxide applied 24 hours after the end of the ischemia.

Figure 2:
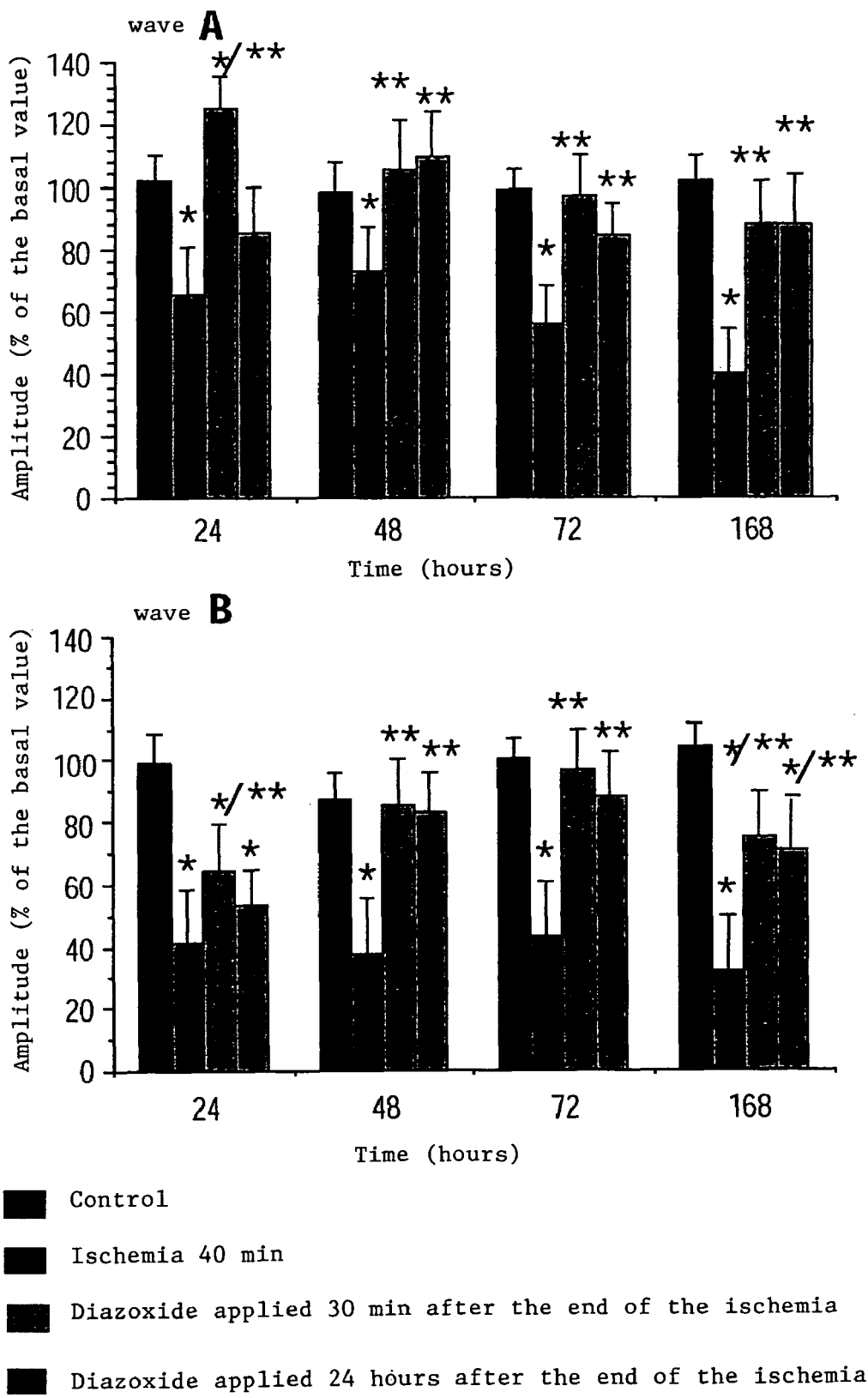
FIGS. 2A and 2B are a pair of graphs showing amplitudes of electroretinogram waves.

FIG. 2 shows the amplitude of waves A (FIG. 2A) and B (FIG. 2B) of the electroretinogram at times 24, 48, 72 and 168 hours for the different groups tested. The different groups tested are:
 i) the control group of control rats not caused to have ischemia and non-treated,
 ii) the group of rats that underwent an ischemia of 40 min but were not treated,
 iii) the group of rats treated by diazoxide applied 30 min after the end of the ischemia, and
 iv) the group of rats treated by diazoxide applied 24 hours after the end of the ischemia.

The values are expressed in percentage of the basal value±the standard deviation (n=7 for each histogram). " . . . " indicates a significant difference between the non-treated group caused to have ischemia or group caused to have ischemia treated with diazoxide and the control group. " . . . " indicates a significant difference between the non-treated group caused to have ischemia or the groups caused to have ischemia treated with diazoxide.

Figure 3:
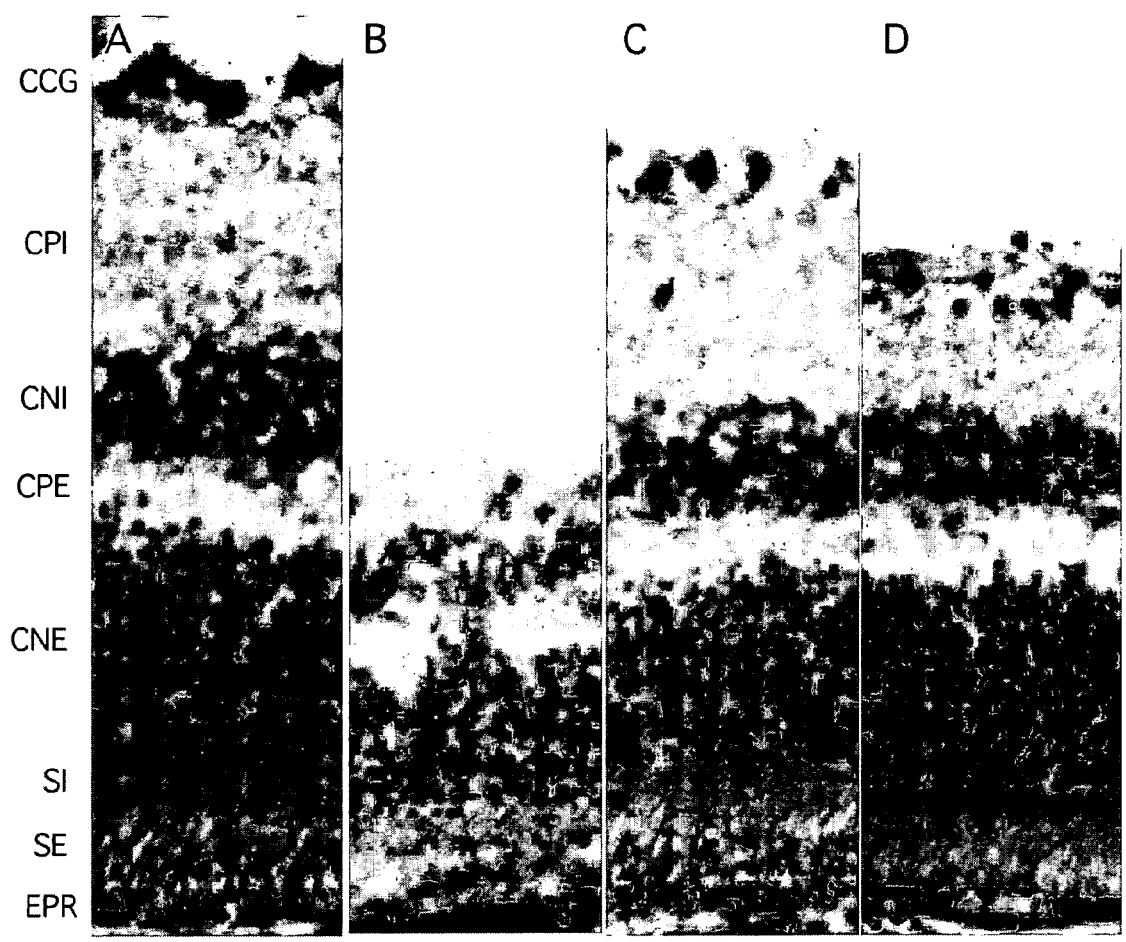
FIGS. 3A-3D are microphotographs of retina samples taken seven days after the end of ischemia in four test groups.

FIG. 3 shows microphotographs representative of the cytoarchitecture of the retina at the time of 7 days after the end of the ischemia in the different groups tested (A to D). FIG. 3A corresponds to the control group (control rats not caused to have ischemia and non-treated), FIG. 3B corresponds to the group of rats that underwent an ischemia of 40 min but were not treated, FIG. 3C corresponds to the group of rats treated by diazoxide applied 30 min after the end of the ischemia, and FIG. 3D corresponds to the group of rats treated by diazoxide applied 24 hours after the end of the ischemia. The abbreviations used are:
 CCG for layer of the ganglionic cells,
 CPI for internal plexiform layer,
 CNI 40 internal nuclear layer,
 CPE for external plexiform layer,
 CNE for external nuclear layer,
 SI for interval segments,
 SE for external segments, and
 EPR for retinal pigmentary epitheliums.

Animals

Brown Norway rats from the scientific stock farm IFFA CREDO with a weight between 200 and 250 g were received and placed into individual cages in an air-conditioned room (temperature between 18 and 20° C.) with a light/dark cycle (12 h/12 h). During the study the animals had free access to food and water.

Local Administration

Diazoxide was dissolved in a pure solution of dimethyl sulfoxide (DMSO). The solution obtained in this manner was diluted in sterile physiological serum to obtain a final ophthalmic solution at 0.01% active principle and 0.4% DMSO.

The local administration was performed by instillation of 10 µl of the ophthalmic solution in the conjunctival cul-de-sac of the right eye 30 minutes after the end of the ischemia for the 1$^{st}$ group and 24 hours after the start of the reperfusion for the second group, then each day for 4 hours.

Induction of the Retinal Ischemia

After general anesthesia of the rats by intraperitoneal injection of sodium pentobarbital (60 mg/kg) the pupil was dilated by instillation of a drop of Mydriaticum®. The anterior chamber of the right eye, previously anesthetized by instillation of a drop of oxybuprocaine, was cannulated with a 30G needle connected to a reservoir containing a Hank's balanced salt solution. The retinal ischemia, lasting 40 min, was induced by elevation of the reservoir containing the saline solution to a height of 185 cm, permitting an intraocular pressure to 130 mm Hg to be produced. Ischemia was characterized by the disappearance of the blood flow in the retinal vessels, determined by direct opthalmoscopy of the ocular fundus. The rats were sacrificed after a period of reperfusion of 7 days. All the rats that developed a cataract or a hemorrhage were separated from the study.

Electrophysiological Analysis

Electroretinography permits evaluation of the retinal function by measuring the electrical activity of the retina and constitutes a tool of choice for the rapid screening of potential molecules allowing the most promising substances in the therapeutic area to be revealed.

The electroretinography is performed under general anesthesia of the rats after dilation of the pupil by instillation of a drop of Mydriaticum®. The animal is previously adapted for 12 hours to darkness, then installed on its flank in a Faraday cage. The measuring electrode, constituted by a silver chloride ring (Ag/AgCl) is placed on the cornea of the right eye. The reference electrode constituted by a silver chloride needle is inserted in the ear of the animal. All these operations are performed under red light.

The luminous stimuli are produced by a stroboscope placed at 25 cm from the eye in the visual axis. The flash of white light lasting 10 µs and with an intensity of $2.5 \cdot 10^3$ $cd \cdot s \cdot m^{-2}$ permits a maximal response of the retina. The recovery of the electrical signal, its amplification, transmission and display on a microcomputer are managed by a compact system. An integrated software permits the acquisition of the data as well as the determination of the amplitudes and of the latency times of the different waves of the electroretinogram (ERG). The ERG in the rat is composed of two waves; a corneo-negative wave or A wave reflecting the activity of the photoreceptors followed by a wave of positive polarity or B wave reflecting the activity of the Müller cells.

The ERG's are recorded for all the groups at time t=0 before induction of ischemia, then at times 1, 2, 3 and 7 days after the start of the reperfusion.

Histological Analysis

On the 7$^{th}$ day of reperfusion the animals were sacrificed by intracardiac injection of an overdose of sodium pentobarbital. The eyes were enucleated, fixed for 2 hours in a solution of 4% paraformaldehyde, then transferred into a solution of 20% sucrose for one night under agitation. The eyes were then enclosed in Tissue-Tek [automatic tissue processor], congealed in isopentane frozen with liquid nitrogen, then stored at −80° C. Cuts of 7 µm were made on a cryostat (Leica), mounted on polylysinated slides dyed blue with toluidine for an analysis of the morphological modifications of the retina.

Statistical Analysis

The pre-ischemic amplitudes of the A and B waves of the ERG are very variable from one group to the other, but also within one and the same group. Recovery is expressed by percentage of the initial value and the difference of effectiveness between each treatment is analyzed with the aid of the U test of Mann Whitney. The significance threshold is 0.02.

Profiles of the Electroretinograms

FIG. 1 compares the profiles of the electroretinograms recorded at time 7 days after the end of the ischemia in the control rats, those caused to have ischemia and not treated and those caused to have ischemia and treated. Compared to the normal ERG of the control group (FIG. 1A), a significant reduction of the B wave, but also of the A wave in the group caused to have ischemia and not treated (FIG. 1B), is observed. This reduction of the electrical activity of the retina is much less drastic in the groups treated with diazoxide (FIG. 1C-1D).

Variations in the Amplitude of the A and B Waves of the Electroretinograms

FIG. 2 shows the variation of the amplitude of the A and B waves recorded at times 24, 28, 72 and 168 hours. In the control rats not caused to have ischemia the amplitude of the A and B waves remains unchanged in the course of time. In the other groups of rats caused to have ischemia variations of the amplitude of the A and B waves at different times of the study are noted.

These variations are characterized in the group caused to have ischemia and not treated by a severe alteration of the electrical activity of the retina. Seven days after the start of the reperfusion the recovery of the amplitude of the A and B waves was respectively equal to 40.55±13.50 and 31.88±18% of the basal values.

Inversely, in the group treated with diazoxide at 0.01%, 30 minutes after the start of the reperfusion and every day for 4 days the recovery was practically total 3 days after the start of the reperfusion. The amplitude of waves A and B was respectively equal to 97.01±13 and 96.36±11%_of the initial values. This recovery declines slightly to attain the respective values of 88.10±14 and 75±14% of the initial values at time 7 days after the end of the ischemia.

The application of diazoxide 24 hours after the start of the reperfusion does not permit a total recovery of the visual function of the retina at time 3 days. Nevertheless, it does permit a better recovery of the electrical activity of the retina compared to the group that was caused to have ischemia and not treated. The values of the amplitude of waves A and B are, respectively, equal to 84.26±10 and 88.17±14% at time 3 days and 87.59±16% and 70.59±16% at time 7 days.

Finally, compared to the non-treated group caused to have ischemia, the statistical analysis shows that diazoxide instilled 30 min or 24 hours after the end of the ischemia has a highly significant effect on the recovery of the retinal function.

Cytoarchitecture of the Retina

FIG. 3 shows the cytoarchitecture of the retina in the different groups. Compared to the "control" group (FIG. 3A), the retina of the non-treated group caused to have ischemia displays a severe attack on the layer of ganglionic cells associated with cellular death and a practically total reduction of the thickness of the internal plexiform layer. The internal nuclear layer, very severely affected, is characterized by the presence of cells scattered in a pyknotic state. In a parallel manner, the photoreceptor layer is characterized by a diminution of the number of rows of nuclei of the photoreceptor cells and by a reduction of the thickness of the internal and external segments (FIG. 3B).

The retinas of the groups treated with diazoxide (FIGS. 3C and 3D) show a less severe reduction of the thickness of the internal plexiform and nuclear layers but also a better preservation of the layers of the ganglionic cells and the photoreceptor cells.

REFERENCES

The subject matter of the references listed below is incorporated herein by reference.

Ashcroft F M, Gribble F M. New windows on the mechanism of action of K(ATP) channel openers. Trends Pharmacol Sci. 2000 November; 21(11): 439-45. Review.

Bernardi H, Fosset M, Lazdunski M. ATP/ADP binding sites are present in the sulfonylurea binding protein associated with brain ATP-sensitive K+ channels. Biochemistry. 1992 Jul. 14; 31(27): 6328-32.

Celebi S, Dilsiz N, Yilmaz T, Kukner A S. Effects of melatonin, vitamin E and octreotide on lipid peroxidation during ischemia-reperfusion in the guinea pig retina. Eur J Ophthalmol. 2002 March-April; 12(2): 77-83.

Chao H M, Osborne N N. Topically applied clonidine protects the rat retina from ischaemia/reperfusion by stimulating alpha(2)-adrenoceptors and not by an action on imidazoline receptors. Brain Res. 2001 Jun. 15; 904(1): 126-36.

Cuevas P, Carceller F, Redondo-Horcajo M, Lozano R M, Gimenez-Gallego G. Systemic administration of acidic fibroblast growth factor ameliorates the ischemic injury of the retina in rats. Neurosci Lett. 1998 Oct. 9; 255(1): 1-4.

Donello J E, Padillo E U, Webster M L, Wheeler L A, Gil D W. alpha(2)-Adrenoceptor agonists inhibit vitreal glutamate and aspartate accumulation and preserve retinal function after transient ischemia. J Pharmacol Exp Ther. 2001 January; 296(1): 216-23.

Duprat F, Lesage F, Patel A J, Fink M, Romey G, Lazdunski M. The neuroprotective agent riluzole activates the two P domain K(+) channels TREK-1 and TRAAK. Mol Pharmacol. 2000 May; 57(5): 906-12.

Ettaiche M, Fillacier K, Widmann C, Heurteaux C, Lazdunski M. Riluzole improves functional recovery after ischemia in the rat retina. Invest Ophthalmol Vis Sci. 1999 March; 40(3): 729-36.

Ettaiche M, Heurteaux C, Blondeau N, Borsotto M, Tinel N, Lazdunski M. ATP-sensitive potassium channels (K(ATP)) in retina: a key role for delayed ischemic tolerance. Brain Res. 2001 Jan. 26; 890(1): 118-29.

Fontaine V, Mohand-Said S, Hanoteau N, Fuchs C, Pfizenmaier K, Eisel U. Neurodegenerative and neuroprotective effects of tumor Necrosis factor (TNF) in retinal ischemia: opposite roles of TNF receptor 1 and TNF receptor 2. J. Neurosci. 2002 Apr. 1; 22(7).

Heurteaux C, Bertaina V, Widmann C, Lazdunski M. K+ channel openers prevent global ischemia-induced expression of c-fos, c-jun, heat shock protein, and amyloid beta-protein precursor genes and neuronal death in rat hippocampus. Proc Natl Acad Sci USA. 1993 Oct. 15; 90(20): 9431-5.

Osborne N N, Wood J P, Cupido A, Melena J, Chidlow G. Topical flunarizine reduces IOP and protects the retina against ischemia-excitotoxicity. Invest Ophthalmol Vis Sci. 2002 May; 43(5): 1456-641.

Seigel G M, Chiu L, Paxhia A. Inhibition of neuroretinal cell death by insulin-like growth factor-1 and its analogs. Mol Vis. 2000 Aug. 31; 6: 157-63.

Szabo M E, Haines D, Garay E, Chiavaroli C, Farine J C, Hannaert P, Berta A, Garay R P L. Antioxidant properties of calcium dobesilate in ischemic/reperfused diabetic rat retina. Eur J. Pharmacol. 2001 Oct. 5; 428(2): 277-86.

Lagreze W A, Muller-Velten R, Feuerstein T J. The neuroprotective properties of gabapentin-lactam. Graefes Arch Clin Exp Ophthalmol. 2001 November; 239(11): 845-9.

The invention claimed is:

1. A method of treating retinal ischemia comprising topically administering to an eye of a mammal a therapeutically effective amount of a pharmaceutical composition comprising diazoxide (7-chloro-3-methyl-21-1-1,2,4-benzothiadiazine-1,1-dioxide) to a mammal.

2. The method according to claim 1, wherein the pharmaceutical composition further comprises riluzole or a derivative active in neuroprotection of the latter or a pharmaceutically acceptable salt of the latter.

3. The method according to claim 1, comprising locally applying the pharmaceutical composition in an eye of the mammal.

4. The method according to claim 1, wherein the pharmaceutical composition is in the form of a collyrium.

5. The method according to claim 1, wherein the diazoxide is applied to a conjunctival sac of the mammal.

6. The method according to claim 1, wherein an ophthalmic solution of the diazoxide is applied.

7. The method according to claim 1, wherein the pharmaceutical composition comprises 0.001 to 0.01%.

\* \* \* \* \*